US00PP22286P2

(12) United States Plant Patent
Danziger

(10) Patent No.: US PP22,286 P2
(45) Date of Patent: Nov. 29, 2011

(54) ***PETUNIA×CALIBRACHOA* PLANT NAMED 'DANCALI3'**

(50) Latin Name: *Petunia sensu Wijsman×Calibrachoa llave*
Varietal Denomination: DANCALI3

(75) Inventor: Gavriel Danziger, Beit Dagan (IL)

(73) Assignee: Danziger 'DAN' Flower Farm

( * ) Notice: Subject to any disclaimer, the term of this patent is extended or adjusted under 35 U.S.C. 154(b) by 0 days.

(21) Appl. No.: 12/802,875

(22) Filed: Jun. 15, 2010

(51) Int. Cl.
*A01H 5/00* (2006.01)

(52) U.S. Cl. ..... Plt./356.11

(58) Field of Classification Search ..... Plt./356.1, Plt./356.11
See application file for complete search history.

*Primary Examiner* — Susan McCormick Ewoldt
(74) *Attorney, Agent, or Firm* — Casandra Bright

(57) ABSTRACT

A new and distinct *PetuniaxCalibrachoa* cultivar named 'DANCALI3 ' is disclosed, characterized by having a distinctive large, bright pink, glossy flowers, and a trailing plant habit. The new variety is a *Petunia sensu Wijsman×Calibrachoa llave* normally produced as an outdoor garden or container plant.

2 Drawing Sheets

Latin name of the genus and species: *Petunia sensu Wijsman×Calibrachoa llave.*

Variety denomination: 'DANCALI3 '.

BACKGROUND OF THE INVENTION

The new *Petunia* cultivar is a product of a planned breeding program conducted by the inventor, Gavriel Danziger, in Moshav Mishmar Hashiva, Israel.

The seed parent is the unpatented, proprietary seedling variety referred to as *Petunia sensu Wijsman* 'Pe-277.' The pollen parent is the unpatented, proprietary seedling variety referred to as *Calibrachoa llave* 'CA793.' The new variety was discovered in March 2008 by the inventor in a group of seedlings resulting from that crossing, in a commercial greenhouse in Moshav Mishmar Hashiva, Israel.

Asexual reproduction of the new cultivar 'DANCALI3' by vegetative cuttings was first performed at a commercial greenhouse in Moshav Mishmar Hashiva, Israel in March 2008 and has shown that the unique features of this cultivar are stable and reproduced true to type in successive generations.

SUMMARY OF THE INVENTION

The cultivar 'DANCALI3' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'DANCALI3.' These characteristics in combination distinguish 'DANCALI3' as a new and distinct *Petunia* cultivar:

1. Distinctive bright pink flower color.
2. Very large flowers.
3. Glossy surface texture of flowers.

Plants of the new cultivar 'DANCALI3' are similar to plants of the seed parent, *Petunia sensu Wijsman* 'Pe-277' in most horticultural characteristics, however, plants of the new cultivar 'DANCALI3' produce larger flowers, of a darker pink and plants with more branches.

Plants of the new cultivar 'DANCALI3' are similar to plants of the pollen parent, *Calibrachoa llave* 'CA-793' in most horticultural characteristics, however, plants of the new cultivar 'DANCALI3' produce bright pink flowers, whereas the pollen parent produces white flowers. Additionally, the new variety produces larger flowers than the pollen parent, and branches less.

COMMERCIAL COMPARISON

Plants of the new cultivar 'DANCALI3' are comparable to the variety 'DANCALIPET,' U.S. Plant Pat. No. 16,063. The two varieties are similar in most horticultural characteristics, however, the new variety 'DANCALI3' differs in having a larger flower, in a solid pink color whereas 'DANCALIPET' has a dark pink/purple flower.

BRIEF DESCRIPTION OF THE PHOTOGRAPH

Figure 1:
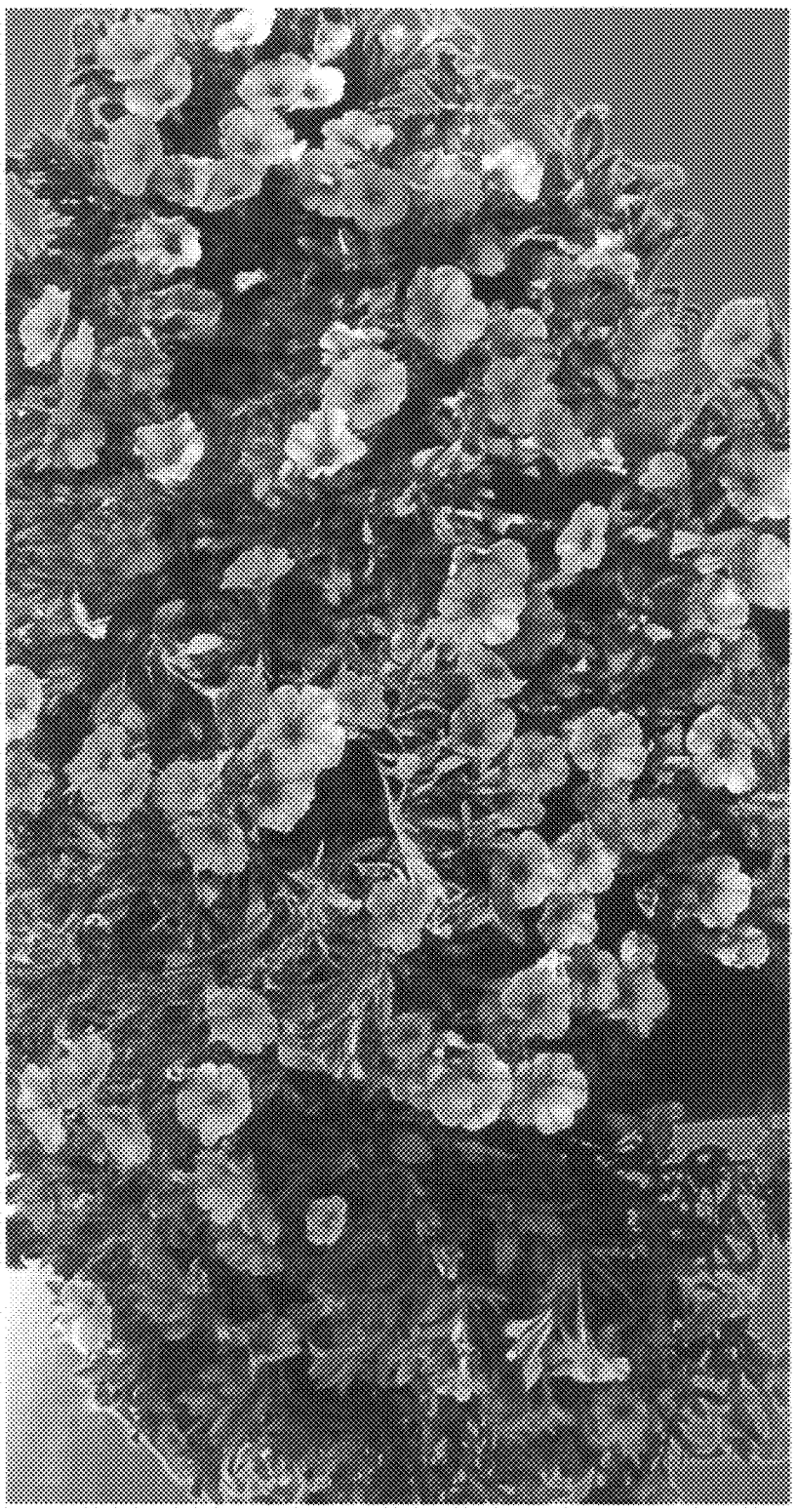

The accompanying photograph in FIG. 1 illustrates in full color a typical plant of 'DANCALI3' grown in a greenhouse, in a 16 cm basket. Age of the plant photographed is approximately 3 months from a rooted cutting.

Figure 2:
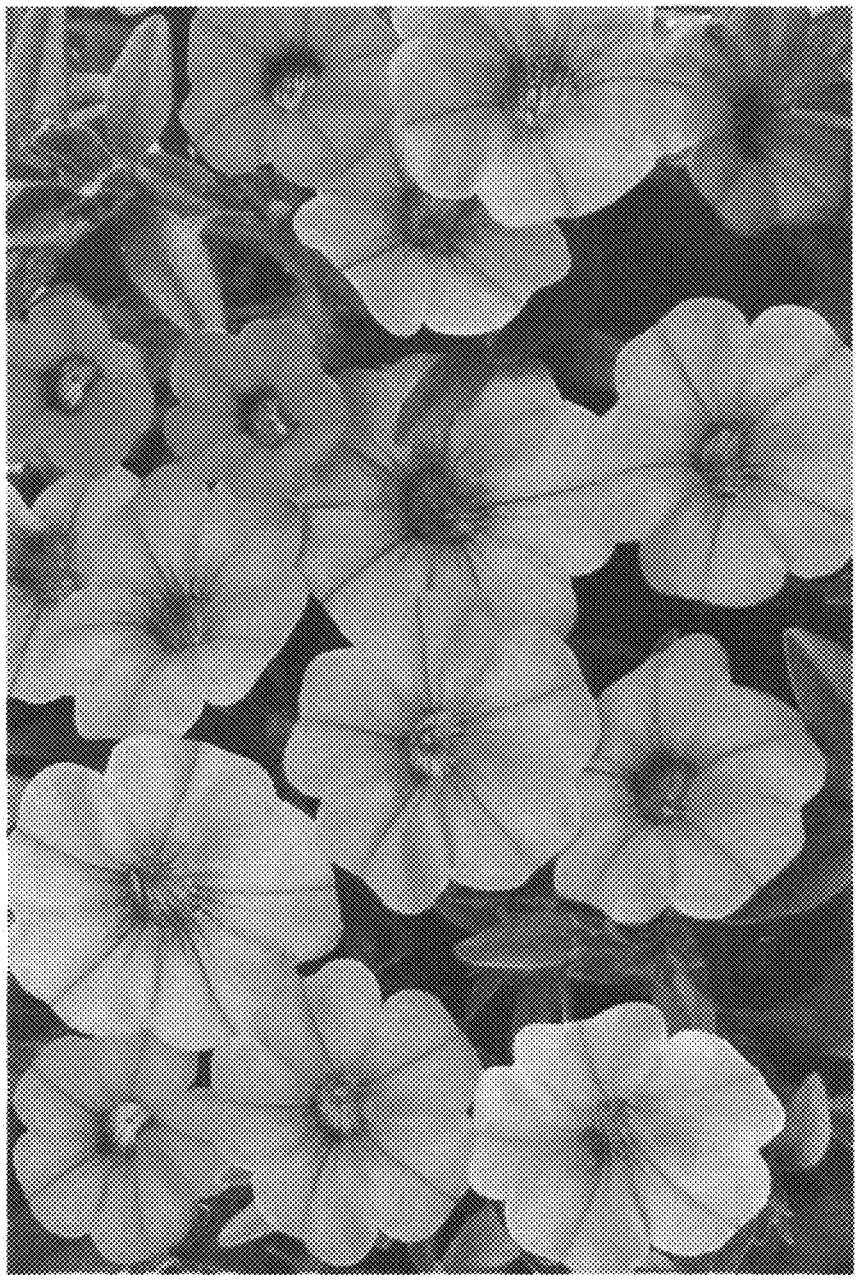

FIG. 2 illustrates in full color a close up of a typical bloom of 'DANCALI3.'

The photographs were taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart except where general terms of ordinary dictionary significance are used. The following observations and measurements describe 'DANCALI3' plants grown outdoors during Autumn in Moshav Mishmar Hashiva, Israel. The growing temperature ranged from 20° C. to 35° C. during the day and from 17° C.

to 23° C. during the night. General light conditions are bright, normal sunlight, with some shade during the brightest part of the day. Measurements and numerical values represent averages of typical plant types.

Botanical classification: *Petunia sensu Wijsman*×*Calibrachoa llave* 'DANCALI3.'

PROPAGATION

Time to initiate roots: About 10 to 14 days at approximately 18-30° C.

Root description: Fine, fibrous.

PLANT

Growth habit: Trailing.

Pot size of plant described: 12 cm.

Age of plant described: Approximately 30 days from a rooted cutting.

Height:

*To top of flowers.*—Approximately 7 cm.

Plant spread: Approximately 20 cm.

Growth rate: Moderate.

Branching characteristics: Very well-branched.

Characteristics of lateral branches:

*Quantity.*—Approximately 15.

*Length.*—Approximately 10 cm.

*Diameter.*—Approximately 0.1 cm.

*Color.*—Near RHS Green 139A.

*Texture.*—Pubescent.

*Strength.*—Flexible.

Internode length: Approximately 1 to 2.5 cm.

FOLIAGE

Leaf:

*Arrangement.*—Opposite.

*Quantity.*—Approximately 20 per branch.

*Average length.*—Approximately 3 cm.

*Average width.*—Approximately 1.3 cm.

*Shape of blade.*—Ovate.

*Apex.*—Obtuse.

*Base.*—Acute.

*Margin.*—Entire.

*Texture of surfaces.*—Pubescent.

*Aspect.*—90° from stem.

*Color.*—Young foliage upper side: Near RHS Green 139A. Young foliage under side: Near RHS Green 139A. Mature foliage upper side: Near RHS Green 139A. Mature foliage under side: Near RHS Green 139A.

*Venation.*—Type: Pinnate. Venation color upper side: Near RHS Green 139A. Venation color under side: Near RHS Green 139A.

*Petiole.*—Not present.

FLOWER

Natural flowering season: Freely flowering all year in Moshav Mishmar Hashiva Israel.

Inflorescence and flower type and habit: Salverform, single with fused petals.

Rate of flower opening: 2 to 3 days from bud to fully opened flower.

Flower longevity on plant: Individual flowers last 3 to 6 days on the plant. Self-Cleaning.

Quantity of flowers: Approximately 20 per plant.

Flower size:

*Diameter.*—Approximately 4.5 cm.

*Flower tube length.*—Approximately 2.5 cm.

*Flower tube diameter at distal end.*—Approximately 0.7 cm.

*Flower tube diameter at proximal end.*—Approximately 0.4 cm.

Petals:

*Length from throat.*—About 2 cm.

*Width.*—About 1.5 cm.

*Quantity.*—5, fused.

*Texture.*—Smooth, highly glossy.

*Apex.*—Obtuse.

*Margin.*—Entire.

Color:

*When opening.*—Upper surface: Near RHS Red-Purple N74C. Lower surface: Near RHS Red-Purple N74D.

*Fully opened.*—Upper surface: Near RHS Red-Purple N74C. Lower surface: Near RHS Red-Purple N74D. Flower throat (inside): Near RHS Yellow-Green 145C. Flower throat, vein: Near RHS Red-Purple 70A. Flower tube (outside): Near RHS Yellow-Green 145C. Flower tube, vein: Near RHS Red-Purple 70A. Petal color, fading to: Near RHS Red-Purple N74C.

Bud:

*Shape.*—Tubular.

*Length.*—Approximately 2.5 cm.

*Diameter.*—Approximately 0.5 cm.

*Color.*—Near RHS Red-Purple 74C.

Calyx/sepals:

*Quantity per flower.*—5.

*Shape.*—Elliptic.

*Length.*—Approximately 1.5 cm.

*Width.*—Approximately 0.13 cm.

*Apex.*—Truncate.

*Base.*—Cuneate.

*Margin.*—Entire.

*Texture.*—Lustrous.

*Color.*—Upper Surface: Near RHS Green 139A. Lower Surface: Near RHS Green 139A.

Peduncle:

*Length.*—Approximately 2.5 cm.

*Diameter.*—Approximately 0.1 cm.

*Color.*—Near RHS Green 139A.

*Orientation.*—45° angle.

Fragrance: None.

REPRODUCTIVE ORGANS

Stamens:

*Number.*—5.

*Filament length.*—Approximately 0.6 cm.

Anthers:

*Length.*—Approximately 0.1 cm.

*Shape.*—Spherical.

*Color.*—RHS Yellow 11A.

*Pollen.*—Color: Near RHS Yellow 12A. Quantity: Abundant.

Pistil:

*Number.*—1.

*Length.*—Approximately 0.7 cm.

*Style.*—Length: Approximately 0.7 cm. Color: Near RHS Green 139C.

*Stigma.*—Shape: Spherical. Color: Near RHS Green 139C. Ovary Color: Near RHS Green 139A.

OTHER CHARACTERISTICS

Seeds and fruits: Numerous minute, fruits, few seeds.

Disease/pest resistance: Neither resistance nor susceptibility to pathogens and pests common to *Petunia* have been observed.

Temperature tolerance: The new variety tolerates temperatures between 5 to 40° C.

What is claimed is:

1. A new and distinct cultivar of *Petunia sensu Wijsman*× *Calibrachoa llave* plant named 'DANCALI3' as herein illustrated and described.

* * * * *